(12) United States Patent
Song et al.

(10) Patent No.: US 9,180,156 B2
(45) Date of Patent: Nov. 10, 2015

(54) COMPOSITION FOR CONTROLLING INCREASE IN BLOOD GLUCOSE

(75) Inventors: Dae-Kyu Song, Daegu (KR); Jinho Lee, Daegu (KR)

(73) Assignee: NUC ELECTRONICS CO., Ltd., Daegu (KR)

(*) Notice: Subject to any disclaimer, the term of this patent is extended or adjusted under 35 U.S.C. 154(b) by 0 days.

(21) Appl. No.: 13/588,467

(22) Filed: Aug. 17, 2012

(65) Prior Publication Data

US 2013/0052285 A1    Feb. 28, 2013

Related U.S. Application Data

(62) Division of application No. 13/055,281, filed as application No. PCT/IB2009/053212 on Jul. 23, 2009, now abandoned.

(60) Provisional application No. 61/083,135, filed on Jul. 23, 2008.

(30) Foreign Application Priority Data

Apr. 20, 2009 (KR) .................. 10-2009-0034119

(51) Int. Cl.
| | | |
|---|---|---|
| A61K 36/82 | (2006.01) | |
| A61K 31/25 | (2006.01) | |
| A23L 1/30 | (2006.01) | |
| A23L 1/307 | (2006.01) | |
| A23L 1/308 | (2006.01) | |

(52) U.S. Cl.
CPC .............. *A61K 36/82* (2013.01); *A23L 1/3002* (2013.01); *A23L 1/307* (2013.01); *A23L 1/3084* (2013.01); *A61K 31/25* (2013.01); *A23V 2002/00* (2013.01)

(58) Field of Classification Search
CPC ............................. A61K 36/82; A61K 31/25
USPC ......................................................... 424/729
See application file for complete search history.

(56) References Cited

U.S. PATENT DOCUMENTS

2006/0263453 A1* 11/2006 Smith et al. .................. 424/729
2007/0036874 A1    2/2007 Zhong

FOREIGN PATENT DOCUMENTS

WO    2007/039262 A1    4/2007
WO    2009/047639 A2    4/2009

OTHER PUBLICATIONS

Anderson et al., "Tea Enhances Insulin Activity," *J. Agric. Food Chem.* 50:7182-7186, 2002.
Arakawa et al., "Improved diabetic syndrome in C57BL/KsJ-db/db mice by oral administration of the Na+-glucose cotransporter inhibitor T-1095," *British Journal of Pharmacology* 132:578-586, 2001.
Bonora, "Protection of pancreatic beta-cells: Is it feasible?" *Nutrition, Metabolism & Cardiovascular Diseases* 18:74-83, 2008.
Chen et al., "Absorption, Distribution, and Elimination of Tea Polyphenols in Rats," *Drug Metabolism and Disposition* 25:1045-1050, 1997.
Chow et al., "Phase I Pharmacokinetic Study of Tea Polyphenols following Single-dose Administration of Epigallocatechin Gallate and Polyphenon E," *Cancer Epidemiol Biomarkers Prev* 10:53-58, 2001.
Collins et al., "Epigallocatechin-3-Gallate (EGCG), a Green Tea Polyphenol, Suppresses Hepatic Gluconeogenesis Through 5'-AMP-Activated Protein Kinase," *J Biol Chem.* 282(41):30143-30149, 2007.
Fukino et al., "Randomized Controlled Trial for an Effect of Green Tea Consumption on Insulin Resistance and Inflammation Markers," *J. Nutr Sci Vitaminol (Tokyo)* 51:335-342, 2005.
Hara et al., "The Inhibition of α-Amylase by Tea Polyphenols," *Agric Biol. Chem.* 54(8):1939-1945, 1990.
Jiang et al., "Hypermethylation of hepatic Gck promoter in ageing rats contributes to diabetogenic potential," *Diabetologia* 51:1525-1533, 2008.
Johnston et al., "Dietary polyphenols decrease glucose uptake by human intestinal Caco-2 cells," *FEBS Letters* 579:1653-1657, 2005.
Kao et al., "Modulation of Endocrine Systems and Food Intake by Green Tea Epigallocatechin Gallate," *Endocrinology* 141:980-987, 2000.
Kim et al., "Cancer's Molecular Sweet Tooth and the Warburg Effect," *Cancer Res* 66:8927-8930, 2006.
Kobayashi et al., "Green Tea Polyphenols Inhibit the Sodium-Dependent Glucose Transporter of Intestinal Epithelial Cells by a Competitive Mechanism," *J. Agric. Food Chem.* 48:5618-5623, 2000.
Lambert et al., "Mechanisms of Cancer Prevention by Tea Constituents," *J. Nutr.* 133:3262S-3267S, 2003.
Lee et al., "Pharmacokinetics of Tea Catechins after Ingestion of Green Tea and ( −)-Epigallocatechin-3-gallate by Humans : Formation of Different Metabolites and Individual Variability," *Cancer Epidemiol Biomarkers Prev* 11:1025-1032, 2002.
Lin et al., "Factors Affecting the Levels of Tea Polyphenols and Caffeine in Tea Leaves," *J. Agric. Food Chem.* 51:1864-1873, 2003.
Naftalin et al., "Interactions of androgens, green tea catechins and the antiandrogen flutamide with the external glucose-binding site of the human erythrocyte glucose transporter GLUT1," *British Journal of Pharmacology* 140:487-499, 2003.
Nomura et al., "Inhibitory Mechanisms of Flavonoids on Insulin-Stimulated Glucose Uptake in MC3T3-G2/PA6 Adipose Cells," *Biol. Pharm. Bull.* 31(7):1403-1409 2008.
Park, "Flavonoids are Potential Inhibitors of Glucose Uptake in U937 Cells," *Biochemical and Biophysical Research Communications* 260:568-574, 1999.
Park et al., "Ambivalent Role of Gallated Catechins in Glucose Tolerance in Humans: A Novel Insight Into Non-Absorbable Gallated Catchin-Derived Inhibitors of Glucose Absorption," *Journal of Physiology and Pharmacology* 60(4):101-109, Dec. 2009.
Polychronopoulos et al., "Effects of black and green tea consumption on blood glucose levels in non-obese elderly men and women from Mediterranean Islands (MEDIS epidemiological study)," *Eur J Nutr* 47:10-16, 2008.

(Continued)

*Primary Examiner* — Susan Hoffman
(74) *Attorney, Agent, or Firm* — Seed IP Law Group PLLC (57) ABSTRACT

The present application describes a composition for blood glucose control containing green tea extracts (GTE) with gallated catechins (GC) and macromolecule to prevent the intestinal absorption of GC.

4 Claims, 8 Drawing Sheets

(56) References Cited

OTHER PUBLICATIONS

Raederstorff et al., "Effect of EGCG on lipid absorption and plasma lipid levels in rats," *Journal of Nutritional Biochemistry* 14:326-332, 2003.

Sabu et al., "Anti-diabetic activity of green tea polyphenols and their role in reducing oxidative stress in experimental diabetes," *Journal of Ethnopharmacology* 83:109-116, 2002.

Shimizu et al., "Regulation of intestinal glucose transport by tea catechins," *BioFactors* 13:61-65, 2000.

Strobel et al., "Myricetin, quercetin and catechin-gallate inhibit glucose uptake in isolated rat adipocytes," *Biochem. J.* 386:471-478, 2005.

Tsuneki et al., "Effect of green tea on blood glucose levels and serum proteomic patterns in diabetic (db/db) mice and on glucose metabolism in healthy humans," *BMC Pharmacology* 4:18, 2004.

Van Amelsvoort et al., "Plasma concentrations of individual tea catechins after a single oral dose in humans," *Xenobiotica* 31(12):891-901, 2001.

Yang et al., "Blood and urine levels of tea catechins after ingestion of different amounts of green tea by human volunteers," *Cancer Epidemiol Biomarkers Prev* 7:351-354, 1998.

Zhu et al., "Pharmacokinetics and system linearity of tea catechins in rat," *xenobiotica*, 31: 51-60, No. 1, 2001.

Bae et al., "Effect of Green Tea Extract/Poly-γ-Glutamic Acid Complex in Obese Type 2 Diabetic Mice," *Diabetes Metab J* 37:196-206, 2013.

Park et al., "Green tea extract with polyethylene glycol-3350 reduces body weight and improves glucose tolerance in *db/db* and high-fat diet mice," *Naunyn-Schmiedeberg's Arch Pharmacol* 386:733-745, 2013.

\* cited by examiner

COMPOSITION FOR CONTROLLING INCREASE IN BLOOD GLUCOSE

CROSS-REFERENCE TO RELATED APPLICATIONS

This application is a divisional of U.S. patent application Ser. No. 13/055,281, filed Apr. 14, 2011 (now abandoned); which is a U.S. National Phase Application of International Application No. PCT/IB2009/053212, filed Jul. 23, 2009; which claims the benefit under 37 U.S.C. §119(e) of U.S. Provisional Patent Application No. 61/083,135, filed Jul. 23, 2008.

International Application No. PCT/IB2009/053212 also claims priority to Korean Application No. 10-2009-0034119, filed Apr. 20, 2009.

These applications are incorporated herein by reference in their entireties.

BACKGROUND

1. Field of the Invention

The present invention relates to catechin-related compositions to lower postprandial blood glucose elevation. The present invention also relates to functional foods for blood glucose control containing green tea extracts (GTE) with gallated catechins (GC) and macromolecules that prevent intestinal absorption of GC. One purpose of this invention is to take blood glucose lowering compositions after a meal without any side effects by inhibiting intestinal glucose absorption as well as lipid absorption using a different mechanism from available hypoglycemic agents.

2. Description of the Related Art

Type 2 diabetes is characterized by two main features: peripheral insulin resistance and beta-cell dysfunction. Both hereditary and environmental factors, such as obesity and prolonged hyperglycemia, may trigger or exaggerate human type 2 diabetes. Hyperglycemia causes both beta-cell damage and peripheral insulin resistance via multiple mechanisms, collectively referred to as glucotoxicity (Borona, 2008). In MODY-2 diabetes, functional defects in glucokinase genes restrict hepatic glucose uptake, bringing about prolongation of postprandial hyperglycemia (Jiang et al., 2008), and eventually result in beta-cell overload. Hence, efforts to minimize postprandial hyperglycemia, as well as fasting blood glucose control, are of importance for the prevention and treatment of type 2 diabetes. Although amylase inhibitors or glucosidase inhibitors are available to date to decrease postprandial hyperglycemia, the usage can induce some gastrointestinal side effects, as they block the conversion to monosaccharide. The leaves of green tea (*Camellia sinensis*) contain polyphenols, in which catechin family is the most major polyphenol. Catechins extracted with water from green tea leaves contain gallated catechins (GC), which mainly include gallate, epicatechin gallate (ECG) and epigallocatechin gallate (EGCG). With regard to type 2 diabetes, the effects of green tea extracts (GTE) or EGCG in in vitro and in vivo studies were intensively investigated. However, the debate over whether GTE or EGCG is actually applicable for the prevention or treatment of human obesity and type 2 diabetes has not been settled (Anderson & Polansky, 2002; Fukino et al., 2005; Naftalin et al., 2003). Daily consumption of green tea by diabetic humans over a period of several months was recently revealed to be ineffective in alleviating blood glucose levels, HbA1C levels, insulin resistance and inflammation markers (Fukino et al., 2005). Interestingly, it has been demonstrated that orally-applied GTE may inhibit glucose (Johnston et al., 2005; Kobayashi et al., 2000; Zhu et al., 2001) and cholesterol (Raederstorff et al., 2003) absorption from the alimentary tract. This is thought to be one of the underlying mechanisms by which GTE influences type 2 diabetes and obesity. Gallated catechins (GC), including EGCG and epicatechin-3-gallate (ECG), appear to be responsible for the inhibitory effects, mainly through the inhibition of Na-glucose co-transporters (SGLT1) in the intestinal epithelia (Kobayashi et al., 2000) and mixed micelle formation in the intestinal lumen (Raederstorff et al., 2003). The amount of GC that needs to be ingested to exert the luminal effect appears to be endurable in humans (Kobayashi et al., 2000; Van Amelsvoort et al., 2001), probably due to the lower oral bioavailability of these molecules. Nevertheless, a certain proportion of the ingested catechins is inevitably absorbed into the blood and acts at other sites within the body. Therefore, the effects of orally-ingested GTE on glucose and lipid metabolism are the combination of the effects in the alimentary tract and in the circulation. Some reports demonstrated that oral application of GTE in rats (Sabu et al., 2002) and humans (Tsuneki et al., 2004) decreased blood glucose levels during an oral glucose tolerance test (OGTT). However, these results could be attributed to the luminal effect of GC (Naftalin et al., 2003) because the high glucose was applied immediately after the catechin ingestion. In addition, as rats have very low oral bioavailability of GTE, during the experiment, it is more difficult to detect the effect of GTE after GTE is absorbed in the circulation. This prompted us to evaluate the effects of GTE and EGCG in the circulation as well as in the alimentary tract.

The inventor discovered that GC in the circulation increased blood glucose levels and thus induced insulin hypersecretion. Therefore, a combinatorial application of GTE with an inhibitor of intestinal GTE absorption could effectively obtain the positive GTE effect in the intestinal lumen to lower postprandial blood glucose elevation.

BRIEF SUMMARY

Prolonged postprandial hyperglycemia is a detrimental factor for type 2 diabetes and obesity. The benefit of green tea extract (GTE) consumption still requires confirmation. We report the effects of circulating green tea catechins on blood glucose and insulin levels. Oral glucose loading 1 h after GTE ingestion in humans led to higher blood glucose and insulin levels than in control subjects. Gallated catechins were required for these effects, although within the intestinal lumen they have been known to decrease glucose and cholesterol absorption. Treatment with epigallocatechin-3-gallate hindered 2-deoxyglucose uptake into liver, fat, pancreatic beta-cell, and skeletal muscle cell lines. Glucose intolerance was ameliorated by gallated catechin-deficient GTE or GTE mixed with polyethylene glycol, which was used as an inhibitor of intestinal absorption of gallated catechins. These findings suggest that gallated catechin when it is in circulation elevates blood glucose level by blocking normal glucose uptake into the tissues, resulting in secondary hyperinsulinemia, whereas it decreases glucose entry into the circulation when they are inside the intestinal lumen. These findings encourage the development of non-absorbable derivatives of gallated catechins for preventative treatment of type 2 diabetes and obesity, which would specifically induce only positive luminal effect.

In one aspect, the invention is directed to a composition for blood glucose control containing green tea extracts (GTE) with gallated catechins (GC) and macromolecule to prevent the intestinal absorption of GC. The GC component may comprise at least one of EGCG or ECG. The macromolecule may be polyethylene glycol (PEG), PEG derivatives, PEG copolymer, water-soluble copolymer, methoxy PEG (mPEG) or polypropylene glycol (PPG). The macromolecule may have a molecular weight of 1,000-2,000,000 daltons.

In another aspect, the invention is directed to a functional food that includes the composition described above. The food may be without limitation beverage, tablet or powder.

In yet another aspect, the invention is directed to a pharmaceutical composition that includes a blood glucose controlling amount of the composition described above, and a pharmaceutically acceptable excipient thereof. The GC may include EGCG or ECG or both. The macromolecule may be PEG, PEG derivatives, PEG copolymer, water-soluble copolymer, methoxy PEG (mPEG) or PPG. The macromolecule may have a preferable molecular weight of 1,000-50,000 daltons.

In another aspect, the invention is directed to a method for controlling blood glucose level in a subject, comprising administering to the subject the composition described above.

These and other objects of the invention will be more fully understood from the following description of the invention, the referenced drawings attached hereto and the claims appended hereto.

BRIEF DESCRIPTION OF THE SEVERAL VIEWS OF THE DRAWINGS

The present invention will become more fully understood from the detailed description given herein below, and the accompanying drawings which are given by way of illustration only, and thus are not limitative of the present invention, and wherein;

FIGS. 1A-1D show ambivalent effects of GTE on glucose tolerance. Changes in blood glucose (A) and plasma insulin (B) levels during human OGTT, which was performed immediately after GTE ingestion. The ingested GTE contained ~500 mg EGCG. n=6 for each group. Changes in blood glucose (C) and plasma insulin (D) levels during human OGTT, which was performed 1 h after GTE ingestion. The ingested GTE contained ~250 mg EGCG. n=5 for each group. Individuals were fasted overnight before the experiments. Control subjects ingested an equivalent amount of water. Two-tailed, unpaired Student's t-test. *P<0.05 and **P<0.01 compared to the control value at the same time point.

FIGS. 2A-2B show effects of circulating GC on glucose tolerance. (A) Changes in blood glucose levels during rat IPGTT, which was performed 30 min after each catechin injection. Rats were fasted for 12 h and then intravenously injected with PBS alone, or PBS containing EC in DMSO, ECG, EGC or EGCG (each 10 mg/kg). Area under the curve (AUC) was depicted in (B) as the percentage of the control value without any catechins. ANOVA with Bonferroni correction. *P<0.05 and **P<0.01 compared to the control value (B) or that of the same time point (A). n=5-7 for each group.

FIGS. 3A-3D show EGCG-mediated decreases in glucose uptake. 2-Deoxy-[$^3$H] glucose was added after a 20-min incubation with the indicated concentrations of EGCG with or without 100 nM insulin in the media containing differentiated L6 myoblasts (A), HepG2 hepatocytes (B), differentiated 3T3-L1 adipocytes (C) and INS-1 beta cells (D). Data are shown as the percentage of each control value in the absence or presence of insulin. *P<0.05, P<0.01, *P<0.001, as compared to the corresponding control without insulin, and $^\#$ P<0.05, $^{\#\#}$ P<0.01, $^{\#\#\#}$ P<0.001, as compared to each control with insulin, using ANOVA with Bonferroni correction. n=3 for each group.

FIGS. 5A-5D show effect of circulating EGCG on blood glucose levels and insulin resistance. EGCG injection (10 mg/kg, i.v.) was performed in 4-h fasted rats (A and C) and Kir6.2 k/o mice (B and D). Control animals received PBS alone. Significant increase in blood glucose level was observed 30 min after EGCG injection. Then insulin (1 IU/kg, i.p.) was injected at the time indicated by the arrows. The percent change in blood glucose levels was shown in C and D; the values of the two groups obtained immediately before the insulin injection were normalized to 100. *P<0.05, P<0.01, *P<0.001, as compared to the control value at the same time point using the two-tailed, unpaired Student's t-test. $^{\#\#}$ P<0.01 refers to the comparison between immediately before and 30 min after EGCG injection, with the two-tailed, paired Student's t-test. n=5 for each group.

FIGS. 6A-6D show that GC-deficient GTE diminishes effects of natural GTE in the circulation and the alimentary tract. (A) In 4-h fasted rats, PBS as control, natural GTE (100 mg/kg) or GC-deficient GTE (100 mg/kg) was intravenously injected 30 min before insulin injection (1 IU/kg, i.p.). (B) The values of the three groups obtained immediately before the insulin injection were normalized to 100. $^\#$ P<0.05 refers to the comparison between immediately before and 30 min after EGCG injection, with the two-tailed, paired Student's t-test. n=5 for each group. (C) Rats were fasted for 12 h, and then intravenously injected with PBS only, or PBS containing natural GTE or GC-deficient GTE 30 min before intraperitoneal high glucose loading. n=5 per group. (D) Rats were fasted for 12 h, and then orally ingested distilled water alone, or distilled water containing natural GTE (900 mg/kg), GC-deficient GTE (900 mg/kg) or EGCG (90 mg/kg) immediately before oral high glucose loading. *P<0.05, P<0.01, *P<0.001, as compared to the control value at the same time point, using ANOVA with Bonferroni correction. n=6 per group.

FIGS. 7A-7D show ingestion of PEG with GTE blocks the circulating effect of GTE. (A) Rats were fasted for 12 h, and then orally ingested distilled water alone (control), or distilled water containing PEG, natural GTE (900 mg/kg), or GTE plus PEG immediately before oral high glucose loading. n=4 for each group. (B) Human volunteers were fasted overnight before the experiments. In the next morning, they ingested water alone, or water containing GTE with 125 mg or 500 mg of EGCG, or PEG plus GTE with 500 mg of EGCG. Oral glucose loading was achieved shortly after the ingestion. n=8-10 for each group. (C and D) In overnight-fasted human volunteers, oral glucose loading was achieved 1 h after the ingestion of water containing GTE with 500 mg of EGCG, or the GTE plus PEG. Control subjects ingested an equivalent amount of water. n=5-6 for each group. *P<0.05, P<0.01 and *P<0.001 as compared to the control value at the same time point, using ANOVA with Bonferroni correction.

FIG. 8 shows an illustration showing the ambivalent effects of GC in the intestine and in circulation. The dotted lines represent movement of the molecules; the solid arrow line represents facilitation by insulin; the solid block lines represent inhibition by GC.

DETAILED DESCRIPTION

In the present application, "a" and "an" are used to refer to both single and a plurality of objects.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "subject" is a mammal, more preferably a human.

The method to manufacture the compositions with blood glucose lowering effect as to this invention contains the step to extract GC, which possesses at least one of either EGCG or ECG, from green tea; the step of mixing the GC-containing extract solution or powder with at least one of polyglycol (PG), such as polyethylene glycol (PEG), PEG derivatives (e.g., PEG-alkyl, PEG-dialkyl, PEG-ester, PEG-diester, etc.), PEG copolymer (e.g., PEG-PPG, PEG-PPG-PEG (poloxamer, Pluronic)), water-soluble copolymer (e.g., polyvinyl pyrrolidine etc.), or macromolecules to selectively bind GC.

The above compositions can also be manufactured by mixing PG with GC which is commercially concentrated and available. The above compositions contain GC at concentrations between 10-2000 mg and PG (0.01-50 g/gGC). The molecular weight of the above PG is 100-2,000,000 daltons, more appropriately 500-100,000 daltons, the most appropriately, 1,000 to 80,000 daltons, 1,000-50,000 daltons, or 1,000 to 8,000 daltons as it is better to be ingested without discomfort and control blood glucose.

According to requested physical properties and nature, the chemical structure of used PG can be various PG derivatives with one or two substitution; C1-C6 alkyl, aryl, acetyl, acetyl substituted for C1-C6alkyl or aryl, sulfone substituted for C1-C6alkyl or aryl on the terminus of PG.

The method to manufacture the above GC include 1. step for filtering the extract solution obtained by boiled water extraction of dry leaves;

2. step for obtaining powder by lyophilizing the above extract solution; and 3. step for purification of GC or its fraction by column chromatography, after dissolving the powder with distilled water.

To describe the details of the above steps, in Step 1, green tea leaves were added to hot water (80-95° C., 10-50 times of leaves weight), stirred gently for 5 min-1 hour for extraction and filtered. In step 2, the powder containing polyphenols of green tea was obtained by lyophilizing the above extract solution. In step 3, to purify and obtain polyphenol chemicals in the powder, column chromatography was performed. This invention employed high porosity polystyrene gel column chromatography (particle size, 75-150 µm, Diaion HP-20, Mitsubishi Kagaku Co., Japan; Column, 25 ɸ×1,000 mm). At this time, the extraction solvent was 100 ml methanol:$H_2O$ (1:5), and the extract was extracted once more with 100 ml methanol:$H_2O$ (2:5). The flow rate was 5 ml/min.

When the components of green tea polyphenol compounds obtained by the above method were analyzed, gallocatechin and epigallocatechin were harvested in Fraction 1. In Fraction 2, catechin, epicatechin, gallocatechin gallate and EGCG were detected. In Fraction 3, ECG was collected.

According to this invention, GC contained in manufactured compositions inhibits the activity of SGLT (sodium-dependent glucose transporter) in the intestinal lumen and thus suppresses intestinal glucose absorption. It has fewer side effects than now available hypoglycemic drug to inhibit amylase activity. In addition, the intestinal absorption of GC itself, which increases blood glucose in the circulation, can be suppressed by co-administered polyglycol (PG). Therefore, this invention, by decreasing postprandial blood glucose levels, may offer diabetic prevention of normal individuals, inhibition of diabetic progression of individuals predisposed to diabetes, and relief of diabetic complications of diabetic patients.

The GC-contained compositions of this invention are applied orally with commercially available types. They can be applied before or during a meal, but preferably to be applied just before a meal.

Because the GC-contained compositions of this invention are natural bioactive materials extracted from natural green tea and not absorbed into the circulation, when orally applied in animals and humans, they are safe without side effects and acute toxicity. Therefore, this invention offers food or functional healthy food, containing GC and PG, to control postprandial blood glucose.

According to this invention, in the case of manufacturing as a pharmaceutical agent, GC and PG can be mixed and formed with commercially and pharmaceutically available material to make tablets, rigid or soft capsules, chewing tablets, powder, liquid or immersion on the purpose of oral ingestion.

In the formation of tablets, rigid or soft capsules, chewing tablets, powder, liquid or immersion as an orally applicable material using the compositions, it can contain Arabian gum, corn starch, bonding material like fine grain cellulose or gellatin, vehicle like calcium phosphate or lactose, disintegrator like alginic acid, corn starch or potato starch, lubricant like stearic acid magnesium, sweetener like sucrose or saccharine, and flavor like methyl salicylate or fruits flavor. In the case of capsule, it can contain liquid materials like fat oil in addition to the above materials.

Potentially all supplementary materials can be mixed and used for the formation of orally applicable materials with GC and PG, if they are pharmaceutically pure, substantially non-toxic, and do not affect the action of bioactive materials.

In this invention, the dose for achieving the effect as a blood glucose controller can be determined by doctors with the consideration in the type of diseases, disease severity, gender, age, body weight, health status, application type, application frequency and time, the presence of combinatorial drugs, and other related environment.

This pharmacological drug in this invention, which contains GC and PG (0.01-50 gram GC), in the case of oral ingestion, 0.5-100 mg EGCG, ECG or its mixed compounds per kg body weight, more appropriately 1-50 mg, can be applied once or several times a day, more appropriately 1-3 times a day, just before, during, or just after a meal.

GC and PG in this invention can be manufactured for a supplementary material of commercial beverages, mineral water, alcoholic beverages, chewing gum, caramel, candy, ice cream, and cookies. In addition, it can be applied in healthy food or food supplements with vitamins and minerals in order to lower postprandial blood glucose.

Discussion of Data

Figure 8:
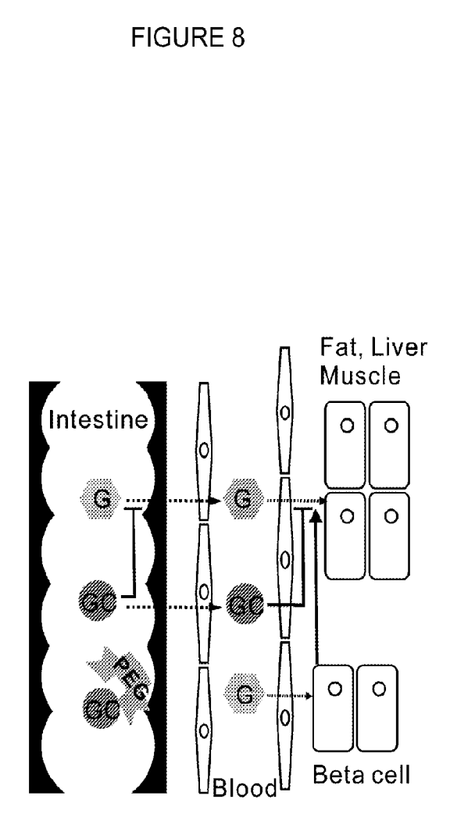

The present study has revealed that GC of green tea, such as EGCG and ECG, acutely reduces blood glucose levels mainly through its activities in the alimentary tract while increases the glucose level when GC is in the circulation (FIG. 8 for summary). Although green tea polyphenols have been reported to inhibit intestinal sucrase and α-amylase activity as well, GC may not be the major inhibitor because the inhibitory effect of green tea was weaker than that of black tea which has a smaller amount of GC (19). The intestinal glucose uptake is mediated by SGLT1, and GTE or GC has been found to be a competitive inhibitor of SGLT1 of human intestinal epithelial cells (9, 20). In the present study, the blood glucose uptake into metabolically-important cells was also inhibited in the presence of EGCG. The inhibitory effect of GC on cellular glucose transporters has been previously observed in mouse adipocytes (21), rat adipocytes (22) and human erythrocytes (7). Hence, one may speculate that GC might hinder the action of various glucose transporters in the body, including the Na-glucose co-transporters as well as the Na-independent glucose transporters. Therefore, GC in the alimentary tract may be helpful in controlling diabetes and obesity by decreasing glucose entry into the circulation (23), but it may be harmful in the circulation. These ambivalent effects of GC in the two compartments may confound attempts to evaluate their precise role in the blood glucose control. We further observed an acute insulin resistance either by circulating EGCG alone or more prominently by circulating GTE. The latter amplification may be due to the other constituents, such as ECG and gallic acid, which may exert additional effects, or may be due to the delayed catabolism of EGCG in the presence of other green tea components (16). Therefore, it is expected that the accumulation of glucose in the circulation caused by green tea catechins may induce insulin hypersecretion. It is not surprising that long-term beta-cell overload represents a detrimental consequence that leads to eventual beta-cell impairment.

In the present study, GTE was effective at blood EGCG concentrations of 1-2 $\mu$M, which is readily achievable by daily oral administration of green tea (24). Experiments that use rats are more likely to overlook this circulating effect, because rats have a much lower oral bioavailability of EGCG (15, 16). To clarify the effect of circulating GTE, we employed long-time OGTT in humans, who have the relatively higher oral bioavailability of EGCG than rats, and found that GTE hindered return of the glucose level to the control value. An in vivo report which examined the circulating EGCG effect within a concentration range applicable to humans showed that relatively long-term intraperitoneal EGCG application led to weight loss in rats (17). However, they found significant deterioration in the sexual organs. It may be probably due to EGCG inhibition of glucose uptake in the androgen-producing Leidig cells (7). A recent investigation (7) revealed that 100 nM ECG competed with glucose for binding to glucose transporter type 1 in red blood cells, such that the reaction rate was half its maximal value. The same effect was attained with 1 $\mu$M EGCG. In this regard, it may be supposed that the decreasing effects on hepatic gluconeogenesis induced by EGCG might be partly due to the EGCG-mediated inhibition of hepatic glucose uptake (7, 25). In addition, the beneficial effects of EGCG in treatment of some cancers may be, at least partly, due to the glucose deprivation effect that EGCG may inflict on cancer cells which are more metabolically active and glycolytic-dependent than normal cells (26). Other polyphenols, such as quercetin and myricetin, seem to have relatively broader safety margins because they inhibit cellular glucose uptake around 10 $\mu$M (27).

The efforts to manage type 2 diabetes and obesity by natural green tea treatment appear to be cautious because systemically-absorbed GC actually blocks cellular glucose uptake and thereby increases blood glucose and insulin levels. Moderate green tea intake (1-2 cups per day) during a meal may be beneficial since the GC entering the circulation will be minimal, but its long-term effect may likely be limited to a certain category of the population (28). Many trials have measured the ability of natural products to inhibit intestinal glucose absorption. However, none of these trials have explored the use of non-absorbable, GC-derived inhibitors of glucose and lipid absorption. Maximizing the positive effect of GC in the intestinal lumen, while minimizing the negative effect in the circulation, would be recommended to control those metabolic diseases.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Materials and Methods

Example 1.1

Materials

Dulbecco's modified Eagle's medium (DMEM), phosphate-buffered saline (PBS), fetal bovine serum (FBS) and fetal calf serum (FCS) were purchased from Gibco (Carlsbad, Calif.). RPMI-1640 medium was purchased from Welgene (Daegu, Korea). Polyethylene glycol (PEG; Novasyn TG hydroxy resin) was delivered from Novabiochem (Darmstadt, Germany) for animal study. PEG for human study was kindly gifted from Taejoon (Seoul, Korea). Green tea leaves (BO-SUNG SEIJAK) were purchased from Bosung green tea Co. (Jeonnam, Korea). Epigallocatechin-3-gallate (EGCG), epi-catechin-3-gallate (ECG), epigallocatechin (EGC) and epi-catechin (EC) were purchased from Sigma-Aldrich (St. Louis, Mo.). All other chemicals were obtained from Sigma-Aldrich.

Example 1.2

Cell Culture

Rat L6 myoblasts were cultured in low-glucose DMEM with 10% (v/v) FBS until they reached 80% confluency. To induce differentiation, cells were further cultured in DMEM (24.9 mM glucose) containing 2% FBS for 7 days. Cell viability was assessed by the trypan blue viability test. Myogenic differentiation to myotube status was evaluated both morphologically and biochemically. Mouse 3T3-L1 preadipocytes were grown to confluence at 37° C. in 35-mm culture dishes in DMEM containing 10% FCS with no added biotin or pantothenate in incubators equilibrated with 5% $CO_2$. At two days post-confluence (day 0), differentiation was induced with methylisobutylxanthine (0.5 mM), dexamethasone (0.5 µM) and insulin (5 µg/ml) in DMEM containing 10% FBS. On day 2, methylisobutylxanthine and dexamethasone were removed and insulin treatment was continued for 2 additional days. On day 4 and thereafter, DMEM (without insulin supplementation) plus 10% FBS was replaced every 2 days. Cells ($2\times10^6$ cells/dish) were used for experiments on day 8. Cell differentiation was evaluated by the Oil red-0 staining. Human hepatocellular carcinoma HepG2 cell line was maintained in DMEM containing 10% FBS at 37° C. Rat insulin-secreting INS-1 cells were grown in RPMI-1640 media supplemented with 10% FBS, 10 mM N-(2-Hydroxyethyl) piperazine-N'-(2-ethanesulfonic acid) (HEPES), 1 mM sodium pyruvate, 50 mM 2-mercaptoethanol, 100 IU/ml penicillin, and 100 mg/ml streptomycin.

Example 1.3

Preparation of GTE

For animal studies, 20 g of green tea leaves were added to 1,000 ml of nanopure water. After being stirred for 5 min at 80° C., the tea leaves were removed by filtration using filter paper (Advantec 2 filter paper, Hyundai micro Co., Seoul, Korea) under reduced pressure. The extract was dried by lyophilization. (A total of 3 g of GTE was harvested, in which EGCG, ECG, EGC and EC were ~100, 53, 56 and 31 mg/g GTE, respectively). An equal amount of the GTE solution was mixed with 2 g PEG bead for 5 min at room temperature. After filtration, the supernatant was lyophilized (EGCG, ECG, EGC and EC were ~26, 14, 42 and 25 mg/g GTE, respectively) to obtain GC-deficient GTE (GTE-GC). The results indicated that the resin pretreatment preferentially reduced GC from the GTE solution. For the human study, 30 g of green tea leaves were added to 500 ml of nanopure water. After being stirred for 3 min at 80° C., tea leaves were removed by filtration, remaining a 350 ml solution, which contained ~500 mg of EGCG.

Example 1.4

OGTT in Humans

Healthy male volunteers aged 20-29 with no family history of diabetes and no insulin resistance judged by Homa index were randomly chosen and fasted overnight before the experiments began. First, individuals who exhibited fasting blood glucose level greater than 100 mg/dl were excluded. At 9:00 AM, each individual orally consumed 350 ml of water only (control), or 350 ml of GTE solution containing 125 mg, 250 mg or 500 mg of EGCG, immediately before or 1-h before ingestion of 150-ml water containing 75 g of glucose. Another group of subjects ingested PEG (110 mg/100 mg EGCG) with the GTE solution. After blood had been collected through an angiocatheter inserted into a forearm vein, blood glucose and plasma insulin levels were measured at the indicated times. Blood glucose levels were measured using the Glucocard test strip II (Arkray Inc., Kyoto, Japan). Plasma insulin levels were measured using an immunoradiometric kit (INSULIN MYRIA, Techno genetics, Sesto, Italy). Before the study began, its purpose and risks were carefully explained, and written informed consent was obtained from all participants. The protocol was approved by the IRB Keimyung University Ethics Committee, Daegu, Korea, regulating human research.

Example 1.5

Intraperitoneal Glucose Tolerance Test (IPGTT) and OGTT in Animals

Sprague-Dawley rats were provided by Hyochang Science Co. (Seoul, Korea). After a 12-h fast, rats were anesthetized using pentobarbital sodium (40 mg/kg, i.p.; Nembutal, 50 mg/ml, Hanlim Pharmaceutical Co., Seoul, Korea) and then injected with one of the epicatechins: EGCG, EGC, ECG, and EC (each 10 mg/kg in 300 µl PBS, i.v.). EC was dissolved in a minute amount of DMSO in advance before addition of PBS. In another experiment, rats were randomly divided into 3 groups: control, GTE and GTE-GC. The rats in the GTE group were injected with natural GTE (100 mg/kg in 300 µl PBS, i.v.; 10 mg/kg as EGCG) through the tail vein, while the control rats were injected with only 300 µl PBS and rats in the GTE-GC group were given an equal amount of GC-deficient GTE (100 mg/kg in 300 μl PBS, i.v.; 2.6 mg/kg as EGCG). Thirty minutes after the injection, glucose (2.0 g/kg in 600 μl distilled water, i.p.) was injected. For OGTT, the rats were ingested with 1-ml distilled water only (control), or 1-ml distilled water containing one of natural GTE (900 mg/kg), GC-deficient GTE (900 mg/kg), EGCG (90 mg/kg), natural GTE plus PEG (110 mg/100 mg EGCG) or PEG alone. Immediately after the ingestion, each rat was orally given 1-ml distilled water containing glucose (2 g/kg). For the assay of blood glucose levels, blood was drawn from the tail vein at the indicated times. All the experiments were approved by the Keimyung University institutional ethics committee, Daegu, Korea for supervising animal research.

Example 1.6

Insulin Tolerance Test (ITT) in Animals

Kir6.2 knock-out (k/o) mice were kindly provided by Prof. Susumu Seino at Kobe University in Japan. Following a 4-h fast, Kir6.2 k/o mice or normal rats were intravenously injected with PBS (100 μl for mouse, 300 μl for rat) only, or PBS containing EGCG (10 mg/kg), natural GTE (100 mg/kg) or GC-deficient GTE (100 mg/kg). Thirty minutes after the injection, the mice and rats were injected intraperitoneally with normal saline (300 μl for mouse, 600 μl for rat) containing insulin (1 IU/kg; INSULIN LISPRO, Eli Lilly, Ind.). Blood samplings were done through the tail vein at the indicated times.

Example 1.7

Deoxyglucose Uptake Assay

Briefly, after serum starvation for 30 min, the cells were washed with Krebs-Ringer phosphate-HEPES buffer [KRPH buffer: 10 mM phosphate buffer, pH 7.4; 1 mM $MgSO_4$, 1 mM $CaCl_2$, 136 mM NaCl, 4.7 mM KCl, and 10 mM HEPES, pH 7.6] and then incubated with or without 100 nM insulin for 20 min in KRPH buffer that contained EGCG (0, 0.1, 1.0 or 10 μM). Glucose transport was determined by the addition of 2-deoxy-[$^3$H] glucose (0.1 mM, 0.5 μCi/ml; PerkinElmer Life and Analytical Science, Waltham, Mass.). After 10 min of incubation, the reaction was stopped by three quick washes with ice-cold PBS. The cells were then lysed in PBS containing 0.2 M NaOH, and glucose uptake was assessed by scintillation counting.

Example 1.8

Western Blot Analysis

To determine the effect of EGCG on the activity of protein kinase B (PKB), the phosphorylation status of PKB was examined after exposure of L6, INS-1, HEPG2 and 3T3L-1 cells to media containing different concentrations of EGCG and insulin. As in the 2-deoxyglucose uptake assay, experimental cells were exposed to media without glucose for 30 min and then incubated with or without 100 nM insulin for 20 min in KRPH that contained EGCG (0, 0.1, 1.0 or 10 μM). After an additional 10 min of incubation with 5 mM glucose, the reaction was stopped by three quick washes with ice-cold PBS. Total cellular proteins were extracted in lysis buffer (10 mM Tris-Cl (pH 7.4), 130 mM NaCl, 5% (v/v) Triton X-100, 5 mM EDTA, 200 nM aprotinin, 20 mM leupeptin, 50 mM phenanthroline, 280 mM benzamidine-HCl) for 20 min at 4° C. Lysates were separated by SDS-PAGE and electrotransferred to an Immobilion-P membrane (Millipore, Billerica, Mass.). After probing with specific antibodies [Anti-phospho-PKB (Ser473) antibody (Cell Signaling Technology, Danvers, Mass.), and anti-β-actin antibody (Sigma)], the immunoreactive bands were visualized with horseradish peroxidase-conjugated secondary antibody (1:5,000; Santa Cruz, Calif.) using enhanced chemiluminescence (Amersham Biosciences, Little Chalfont, UK).

Example 1.9

Analysis of Catechins from GTE with HPLC

HPLC analysis was conducted on a Waters Alliance 2695 liquid chromatograph equipped with a model 2487 dual absorbance detector (Waters Co., Milford, Mass.). A Waters symmetry C18 reversed-phase packing column (4.5 mm×250 mm, 5 μm) was used at 25° C. for separation throughout this study. Catechins were determined simultaneously at 235 nm. A gradient elution was performed by varying the proportion of solvent A (water-trifluoroacetic acid, 99.9:0.1 v/v) to solvent B (acetonitrile-trifluoroacetic acid, 99.9:0.1 v/v), with a flow rate of 1 ml/min. The mobile phase composition changed linearly from 9.5% to 14% solvent B in 10 min and then kept the same composition for 10 min, followed by a linear increase of solvent B to 27.5% within 15 min. The mobile phase composition was then brought back to the initial conditions over a period of 5 min for the next run. All the prepared solutions were filtered through 0.45 μm membranes (Sartorius, Maisemore, UK), and the mobile phase was degassed before injection into the HPLC.

Example 1.10

Statistical Analyses

The results are expressed as mean±SEM. The SPSS (release 14.0) software package (SPSS Inc., Chicago, Ill.) was used for the statistical analyses. Area under the curve was calculated by using Microcal Origin software (version 7.0; Northampton, Mass.). Comparisons between two groups were performed with the Student's two-tailed t-test for paired or unpaired data. For comparisons of more than two groups, significance was tested using an analysis of variance (ANOVA) with Bonferroni correction to deal with relatively small amounts of samples. Differences between groups were considered significant when $P<0.05$.

Example 2

Results

Example 2.1

Figure 1:
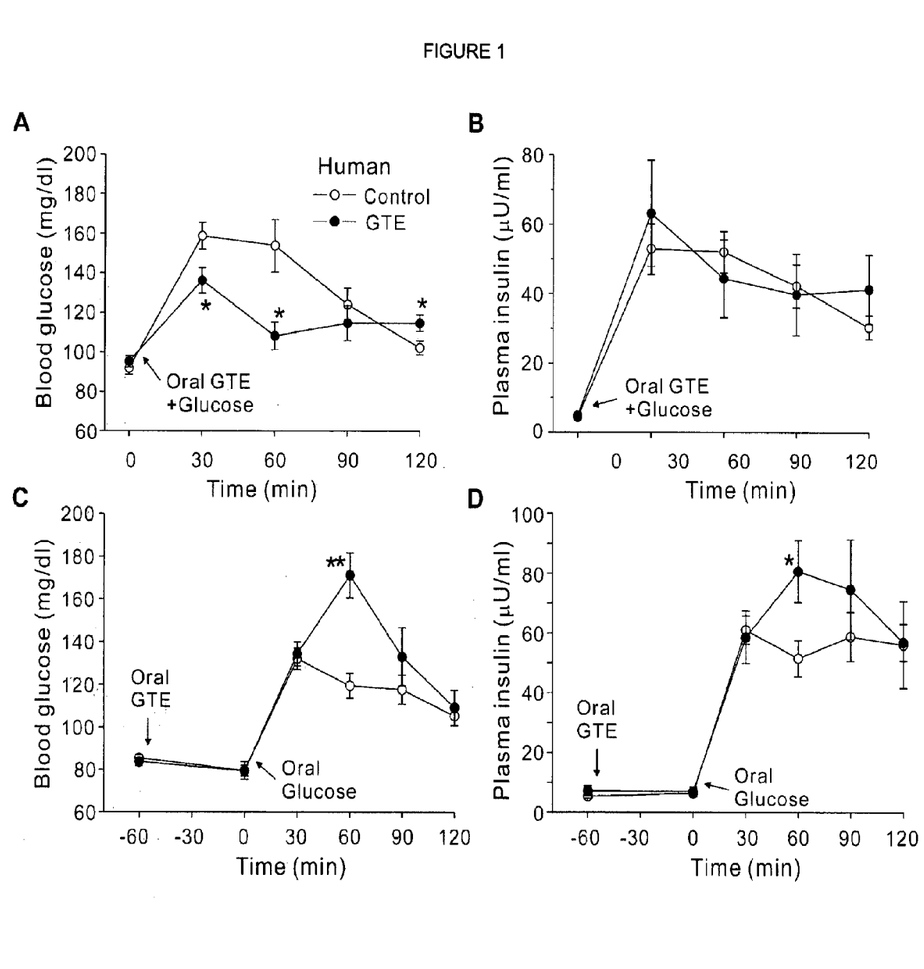

Effect of GTE Intake on Blood Glucose and Plasma Insulin Levels During Human OGTT The results of OGTT that had been performed with healthy male volunteers showed that the effects of GTE intake on glucose tolerance were changed depending on the time lag between GTE and glucose administration. Orally-administered GTE maintained blood glucose levels lower than the control during OGTT when glucose was taken immediately after GTE administration (FIG. 1A). This effect is the same with the previously reported results (14). The lowering effect of GTE on blood glucose levels during OGTT was reversed when it was administered 1 h earlier than the administration of glucose (FIG. 1C). The blood glucose level was significantly higher in the GTE group than in the control 60 min after glucose loading (P<0.01). The 1-h interval between GTE and glucose intake was chosen because the blood concentrations of tea ingredients, especially catechins, were known to peak between 1-2 h after GTE ingestion (4, 15). Interestingly, plasma insulin levels were also significantly (P<0.05) higher in the GTE group at the 60 min (FIG. 1D), implying that the higher blood glucose levels may induce a higher rate of insulin secretion.

Example 2.2

EGCG and ECG of Tea Catechins are Critical for Glucose Intolerance

Figure 2:
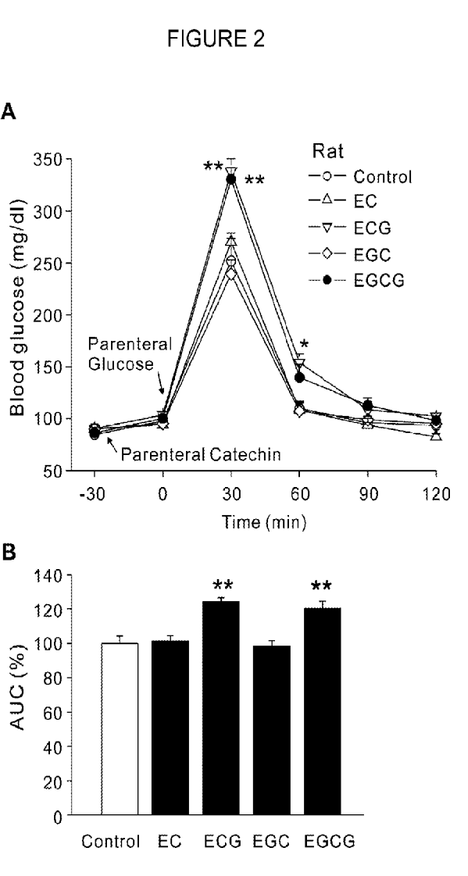

To clarify which GTE components were responsible for the abnormal OGTT in humans, IPGTT was performed with rat (FIG. 2). Since epicatechins were studied intensively for its role in glucose tolerance, EGCG, ECG, EGC and EC were used for IPGTT. Each catechin was injected in rats 30 min before glucose administration. The amount of EGCG injected (10 mg/kg, i.v.) was chosen to achieve its blood concentrations around 1 µM at 30 min after injection (16, 17). Same amount of other catechins was used even though they had different pharmacokinetic profiles (10). EGCG and ECG caused more elevated blood glucose levels 30 min after glucose loading compared to control (P<0.01) while EC and EGC had no effects. This result suggested that the effect of GTE on glucose intolerance was mainly due to the two GC, EGCG and ECG. Since the amount of EGCG in water-soluble GTE was about 2-3 times higher than ECG (18), further studies were performed with EGCG as a representative of GC.

Example 2.3

2-Deoxy-[$^3$H]-Glucose Uptake into Cells is Hindered by EGCG

Figure 3:
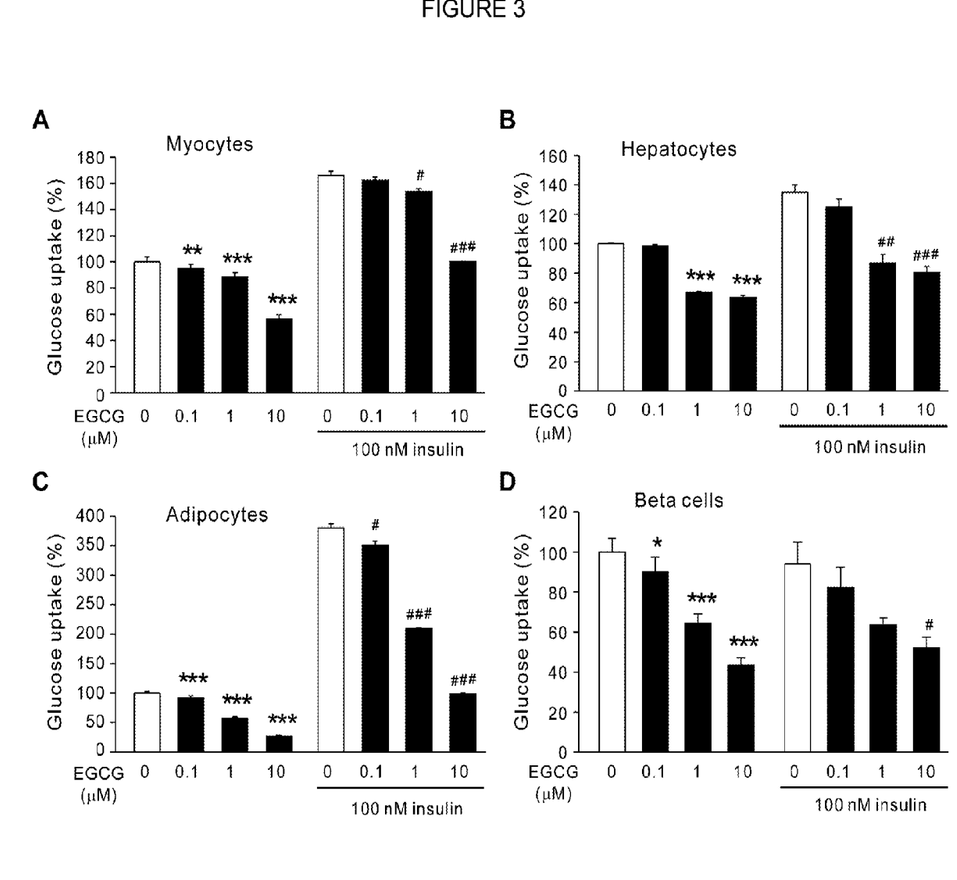
Figure 4:
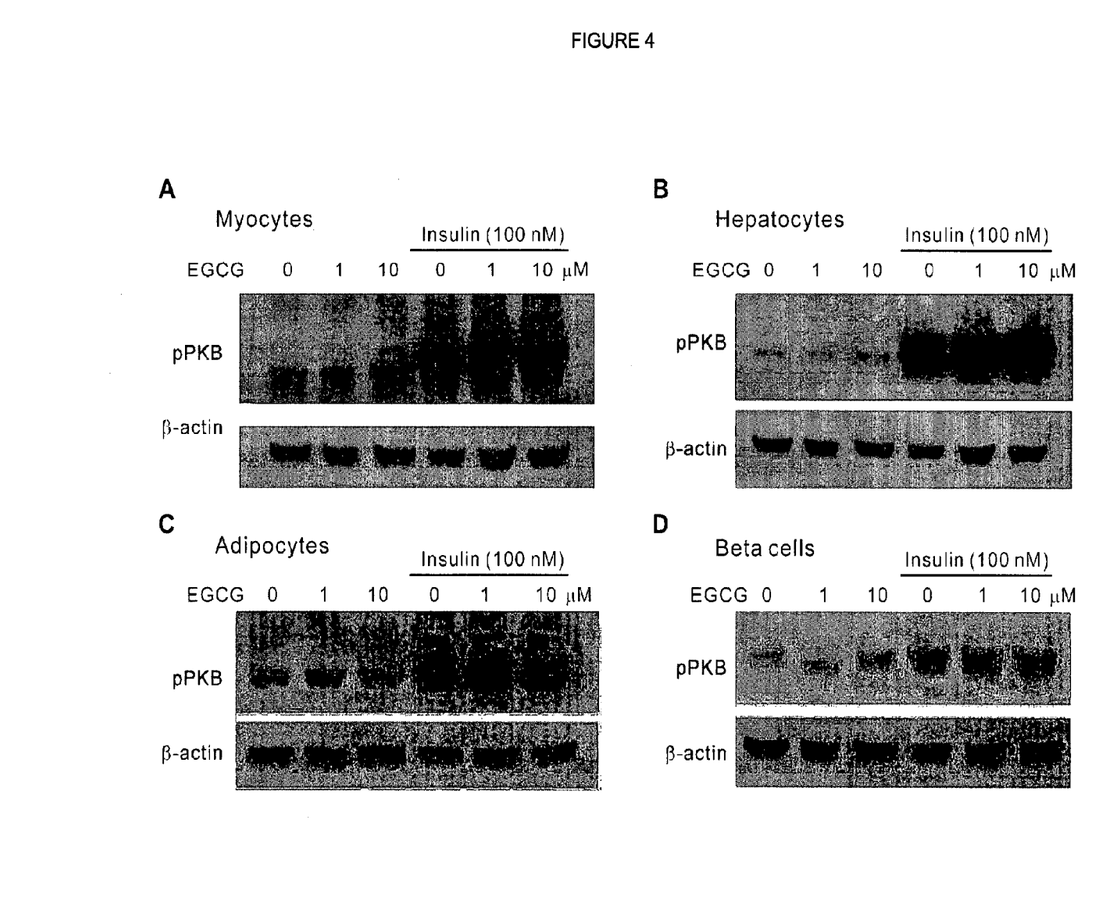
FIGS. 4A-4D show representative data showing that neither basal nor insulin-stimulated PKB phosphorylation is altered by pretreatment with EGCG in differentiated L6 myoblasts (A), HepG2 hepatocytes (B), differentiated 3T3-L1 adipocytes (C) and INS-1 beta cells (D).

The dose dependencies of basal and insulin-stimulated glucose uptake on EGCG were evaluated with metabolically-important cells including beta cells (FIG. 3). Both basal and insulin-stimulated glucose uptake were decreased by EGCG dose-dependently for all EGCG-pretreated cells. Also, in the tested cell lines up to 10 µM EGCG, EGCG did not alter the basal and insulin-regulated expression of phospho-PKB (FIG. 4).

Example 2.4

Figure 5:
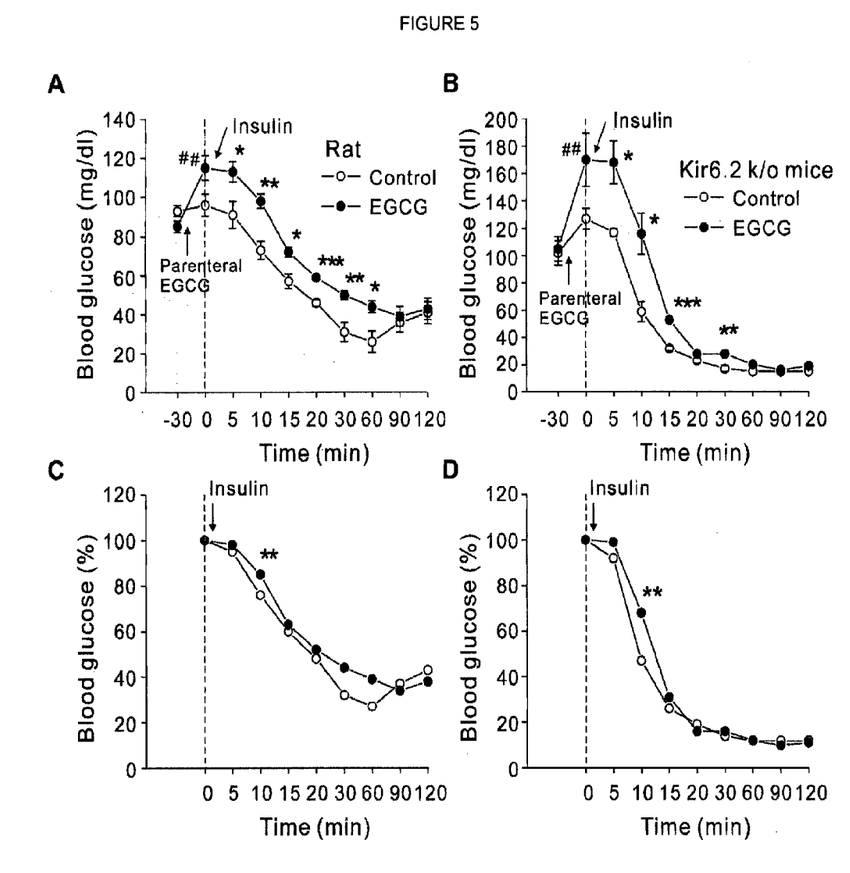

Circulating EGCG Acutely Increases Blood Glucose Levels and Insulin Resistance The possibility of association between EGCG-mediated glucose intolerance and ATP-sensitive potassium ($K_{ATP}$) channels, which modulate peripheral insulin resistance as well as beta-cell insulin secretion, was examined Normal rats and Kir6.2 k/o mice were fasted for 4 h before EGCG injection. The significant elevation of blood glucose levels in both normal rats and Kir6.2 k/o mice were found 30 min after the EGCG injection (P<0.01; FIG. 5A, B). This result suggests that the EGCG-induced change in blood glucose level was not mediated through a mechanism involving $K_{ATP}$ channels. When treated with insulin, the rate of blood glucose disappearance was delayed mildly but significantly in EGCG-pretreated rats and Kir6.2 k/o mice (P<0.01; FIG. 5C, D).

Example 2.5

Effect of GC-Deficient GTE

Figure 6:
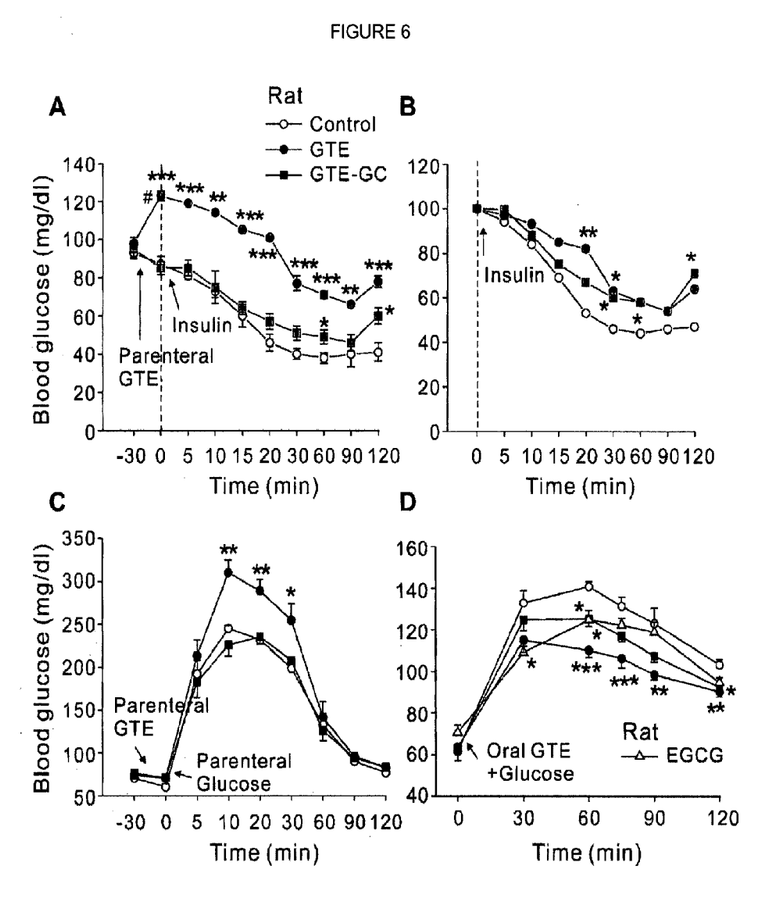

GTE injection with 4-h fasted rats caused significant elevation of blood glucose levels (P<0.05; FIG. 6A), which was similar finding to the injection with EGCG alone in FIG. 5A, while GC-deficient GTE injection did not (P=0.114). ITT revealed remarkable insulin resistance in the GTE group (P<0.01 at the 20 min), whereas significant amelioration of insulin resistance was observed in the GTE-GC group (FIG. 6B). Rats in another experiment were fasted for 12 h, not 4 h, to minimize elevation of blood glucose level by GTE itself. Then they were injected intravenously with PBS alone, or with PBS containing either natural GTE or GC-deficient GTE 30 min before glucose loading. As shown in FIG. 6C, blood glucose levels in the GTE-treated group during IPGTT were remarkably higher than those in the PBS control (P<0.01 at 10 and 20 min), while the GTE-GC group showed similar glucose levels to the control. The effects on glucose absorption into the circulation of GC within the gastrointestinal tract were evaluated by rat OGTT. It was performed by oral intake of GTE immediately followed by glucose ingestion (FIG. 6D). Expectedly, the blood glucose levels were maintained during OGTT at a lower level in the GTE-administered group than in the control group that ingested only PBS. The GC-deficient GTE- or EGCG-administered group appeared to inhibit glucose absorption less efficiently than in the GTE-treated group, indicating that GC is also critical for the effect of GTE on blockade of glucose absorption in the intestinal lumen.

Example 2.6

Effect of Administration of PEG with GTE

Figure 7:
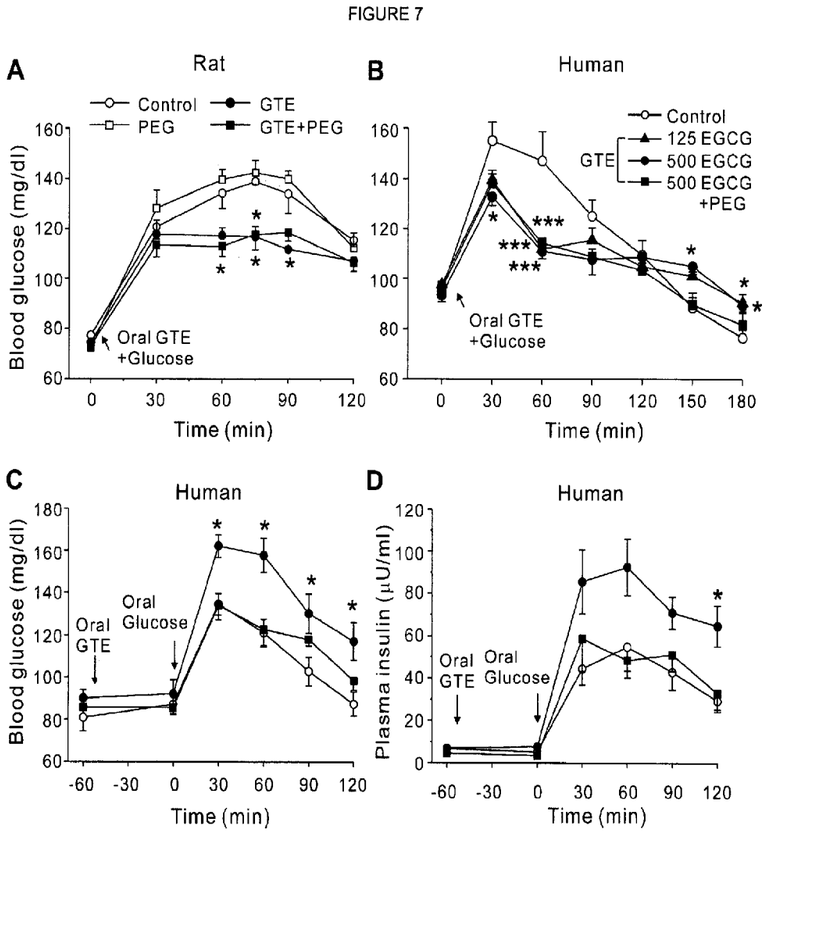

On the assumption that the resin PEG selectively inhibits the intestinal absorption of GC of GTE, natural GTE was ingested along with PEG. During rat OGTT immediately following the ingestion, blood glucose levels were significantly lower in the GTE+PEG group than in the control (P<0.05), comparable to the group with GTE alone (FIG. 7A). There was no difference between the control group and the PEG-alone-treated group in blood glucose levels, indicating that PEG itself did not affect glucose absorption or intestinal motility at the range of concentrations used. The time for human OGTT was extended to 3 h observing the effect of circulating GC on basal blood glucose levels (FIG. 7B). Although the blood glucose levels in the GTE group during the earlier period of OGTT appeared to be lower than in the control, they during the later period of OGTT were significantly higher than in the control, which was not observed in the GTE+PEG group. When human OGTT was conducted 1 h after GTE+PEG ingestion, blood glucose and plasma insulin levels were also normalized in contrast to the GTE group, which showed significant elevation of the glucose and insulin levels (FIG. 7C, D).

Example 3

Manufacturing of Green Tea Extracts and Powder

For animal studies, 20 g of green tea leaves were added to 1,000 ml of nanopure water. After being stirred for 5 min at 80° C., the tea leaves were removed by filtration using filter paper (Advantec 2 filter paper, Hyundai micro Co., Seoul, Korea) under reduced pressure. The extract was dried by lyophilization. (A total of 3 g of GTE was harvested, in which EGCG, ECG, EGC and EC were ~100, 53, 56 and 31 mg/g GTE, respectively)

Example 4

Manufacturing of GC-Deficient GTE Powder

After Example 3, an equal amount of the GTE solution was mixed with 2 g PEG (3,000-4,000) bead for 5 min at room temperature. After filtration, the supernatant was lyophilized (EGCG, ECG, EGC and EC were ~26, 14, 42 and 25 mg/g GTE, respectively) to obtain GC-deficient GTE (GTE-GC). The results indicated that the resin pretreatment preferentially reduced GC from the GTE solution.

Example 5

Manufacturing of Green Tea Extracts and Powder

For the human study, 30 g of green tea leaves were added to 500 ml of nanopure water. After being stirred for 3 min at 80° C., tea leaves were removed by filtration, remaining a 350 ml solution, which contained ~500 mg of EGCG and ~260 mg of ECG.

Example 6

Manufacturing of Pharmaceutical Compositions

Example 6-1

Tablets

A tablet containing 50 mg of EGCG, ECG or its mixed form; 50 mg PEG (4,000); 20 mg starch; adequate amount of stearic acid magnesium can be made as a blood glucose controller, according to general instruction for tablet production.

Example 6-2

Capsules

A capsule filled with 50 mg of EGCG, ECG or its mixed form; 50 mg PEG (4,000); 19 mg starch; 1 mg talc; adequate amount of stearic acid magnesium can be made as a blood glucose controller, according to general instruction for capsule production.

Example 6-3

Granules

A granule can also be made as a blood glucose controller, according to general instruction for granule production.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims References 1. Bonora E. Protection of pancreatic beta-cells: is it feasible? *Nutr Metab Cardiovasc Dis* 2008; 18: 74-83.
2. Jiang M H, Fei J, Lan M S, et al. Hypermethylation of hepatic Gck promoter in ageing rats contributes to diabetogenic potential. *Diabetologia* 2008; 51: 1525-1533.
3. Lambert J D, Yang C S. Mechanisms of cancer prevention by tea constituents. *J Nutr* 2003; 133 (Suppl): S3262-S3267.
4. Yang C S, Chen L, Lee M J, Balentine D, Kuo M C, Schantz S P. Blood and urine levels of tea catechins after ingestion of different amounts of green tea by human volunteers. *Cancer Epidemiol Biomarkers Prev* 1998; 7: 351-354.
5. Anderson R A, Polansky M M. Tea enhances insulin activity. *J Agric Food Chem* 2002; 50: 7182-7186.
6. Fukino Y, Shimbo M, Aoki N, Okubo T, Iso H. Randomized controlled trial for an effect of green tea consumption on insulin resistance and inflammation markers. *J Nutr Sci Vitaminol (Tokyo)* 2005; 51: 335-342.
7. Naftalin R J, Afzal I, Cunningham P, et al. Interactions of androgens, green tea catechins and the antiandrogen flutamide with the external glucose-binding site of the human erythrocyte glucose transporter GLUT1. *Br J Pharmacol* 2003; 140: 487-499.
8. Johnston K, Sharp P, Clifford M, Morgan L. Dietary polyphenols decrease glucose uptake by human intestinal Caco-2 cells. *FEBS Lett* 2005; 579: 1653-1657.
9. Kobayashi Y, Suzuki M, Satsu H, et al. Green tea polyphenols inhibit the sodium-dependent glucose transporter of intestinal epithelial cells by a competitive mechanism. *J Agric Food Chem* 2000; 48: 5618-5623.
10. Zhu M, Chen Y, Li R C. Pharmacokinetics and system linearity of tea catechins in rat. *Xenobiotica* 2001; 31: 51-60.
11. Raederstorff D G, Schlachter M F, Elste V, Weber P. Effect of EGCG on lipid absorption and plasma lipid levels in rats. *J Nutr Biochem* 2003; 14: 326-332.
12. Van Amelsvoort J M, Van H of K H, Mathot J N, Mulder T P, Wiersma A, Tijburg L B. Plasma concentrations of individual tea catechins after a single oral dose in humans. *Xenobiotica* 2001; 31: 891-901.
13. Sabu M C, Smitha K, Kuttan R. Anti-diabetic activity of green tea polyphenols and their role in reducing oxidative stress in experimental diabetes. *J Ethnopharmacol* 2002; 83: 109-116.
14. Tsuneki H, Ishizuka M, Terasawa M, Wu J B, Sasaoka T, Kimura I. Effect of green tea on blood glucose levels and serum proteomic patterns in diabetic (db/db) mice and on glucose metabolism in healthy humans. *BMC Pharmacol* 2004; 4: 18-27.
15. Lee M J, Maliakal P, Chen L et al. Pharmacokinetics of tea catechins after ingestion of green tea and (−)-epigallocatechin-3-gallate by humans: formation of different metabolites and individual variability. *Cancer Epidemiol Biomarkers Prev* 2002; 11: 1025-1032.
16. Chen L, Lee M J, Li H, Yang C S. Absorption, distribution, elimination of tea polyphenols in rats. *Drug Metab Dispos* 1997; 25: 1045-1050.
17. Kao Y H, Hiipakka R A, Liao S. Modulation of endocrine systems and food intake by green tea epigallocatechin gallate. *Endocrinology* 2000; 141: 980-987.
18. Lin Y S, Tsai Y J, Tsay J S, Lin J K. Factors affecting the levels of tea polyphenols and caffeine in tea leaves. *J Agric Food Chem* 2003; 51: 1864-1873.
19. Hara Y, Honda M. The inhibition of α-amylase by tea polyphenols. *Agric Biol Chem* 1990; 54: 1939-1945.

20. Shimizu M, Kobayashi Y, Suzuki M, Satsu H, Miyamoto Y. Regulation of intestinal glucose transport by tea catechins. *BioFactors* 2000; 13: 61-65.

21. Nomura M, Takahashi T, Nagata N, et al. Inhibitory mechanisms of flavonoids on insulin-stimulated glucose uptake in MC3T3-G2/PA6 adipose cells. *Biol Pharm Bull* 2008; 31: 1403-1409.

22. Strobel P, Allard C, Perez-Acle T, Calderon R, Aldunate R, Leighton F. Myricetin, quercetin and catechin-gallate inhibit glucose uptake in isolated rat adipocytes. *Biochem J* 2005; 386: 471-478.

23. Arakawa K, Ishihara T, Oku A, et al. Improved diabetic syndrome in C57BL/KsJ-db/db mice by oral administration of the $Na^+$-glucose cotransporter inhibitor T-1095. *Brit J Pharm* 2001; 132: 578-586.

24. Chow H H, Cai Y, Alberts D S, et al. Phase I pharmacokinetic study of tea polyphenols following single-dose administration of epigallocatechin gallate and polyphenon E. *Cancer Epidemiol Biomarkers Prev* 2001; 10: 53-58.

25. Collins Q F, Liu H Y, Pi J, Liu Z, Quon M J, Cao W. Epigallocatechin-3-gallate (EGCG), a green tea polyphenol, suppresses hepatic gluconeogenesis through 5'-AMP-activated protein kinase. *J Biol Chem* 2007; 282: 30143-30149.

26. Kim J W, Dang C V. Cancer's molecular sweet tooth and the Warburg effect. *Cancer Res* 2006; 66: 8927-8930.

27. Park J B. Flavonoids are potential inhibitors of glucose uptake in U937 cells. Biochem Biophys Res Commun 1999; 260: 568-574.

28. Polychronopoulos E, Zeimbekis A, Kastorini C M, et al. Effects of black and green tea consumption on blood glucose levels in non-obese elderly men and women from Mediterranean Islands (MEDIS epidemiological study). *Eur J Nutr* 2008; 47: 10-16.

The invention claimed is:

1. A method for lowering blood glucose level in a human subject in need of lowering blood glucose level, comprising administering to the human subject a composition containing green tea extracts (GTE) with gallated catechins (GC) and a macromolecule to prevent the intestinal absorption of GC, wherein the macromolecule is polyethylene glycol (PEG), PEG-alkyl, PEG-dialkyl, PEG-ester, PEG-diester, PEG copolymer, methoxy PEG (mPEG) or polypropylene glycol (PPG).

2. The method of claim 1, wherein the GC comprises at least one of epigallocatechin gallate (EGCG) or epicatechin gallate (ECG).

3. The method of claim 1, wherein the macromolecule has a molecular weight of 1,000-2,000,000 daltons.

4. The method of claim 3, wherein the macromolecule has a molecular weight of 1,000-50,000 daltons.

\* \* \* \* \*